United States Patent
Segura-Orsoni et al.

(10) Patent No.: US 8,551,504 B2
(45) Date of Patent: Oct. 8, 2013

(54) TOPICAL ANTI-INFLAMMATORY COMPOSITIONS COMPRISING O/W EMULSIONS CONTAINING PRO-PENETRATING GLYCOLS

(75) Inventors: Sandrine Segura-Orsoni, Mandelieu (FR); Sophie Roumec, Grasse (FR)

(73) Assignee: Galderma S.A., Cham (CH)

( * ) Notice: Subject to any disclaimer, the term of this patent is extended or adjusted under 35 U.S.C. 154(b) by 983 days.

(21) Appl. No.: 12/232,305

(22) Filed: Sep. 15, 2008

(65) Prior Publication Data

US 2009/0104132 A1    Apr. 23, 2009

Related U.S. Application Data

(63) Continuation of application No. PCT/FR2007/050927, filed on Mar. 14, 2007.

(30) Foreign Application Priority Data

Mar. 15, 2006    (FR) ..................................... 06 02284

(51) Int. Cl.
*A61K 9/00*    (2006.01)
*A61K 8/02*    (2006.01)
*A61K 31/52*    (2006.01)
*A01N 45/00*    (2006.01)

(52) U.S. Cl.
USPC ........... 424/400; 424/401; 514/169; 514/180; 514/938; 514/944

(58) Field of Classification Search
USPC ................. 424/400, 401; 514/169, 180, 938, 514/944
See application file for complete search history.

(56) References Cited

U.S. PATENT DOCUMENTS

| | | | |
|---|---|---|---|
| 4,244,942 A | 1/1981 | Kamishita et al. | |
| 4,370,322 A | 1/1983 | Busse et al. | |
| 4,383,986 A * | 5/1983 | Dubash et al. | 424/443 |
| 5,686,086 A | 11/1997 | Yanagida et al. | |
| 6,106,848 A | 8/2000 | Preuilh et al. | |
| 6,410,062 B1 * | 6/2002 | Callaghan et al. | 424/764 |
| 6,767,534 B1 | 7/2004 | Ortiz et al. | |
| 2003/0186951 A1 * | 10/2003 | Gans et al. | 514/174 |
| 2004/0156870 A1 | 8/2004 | Glassman et al. | |
| 2004/0202725 A1 * | 10/2004 | Dascalu | 424/673 |
| 2004/0225140 A1 * | 11/2004 | Fernandez et al. | 552/500 |
| 2006/0052353 A1 | 3/2006 | Johnson | |
| 2008/0207570 A1 * | 8/2008 | Segura-Orsoni | 514/168 |
| 2009/0104131 A1 * | 4/2009 | Segura-Orsoni et al. | 424/59 |
| 2010/0144686 A1 * | 6/2010 | Segura-Orsoni et al. | 514/171 |

FOREIGN PATENT DOCUMENTS

| | | |
|---|---|---|
| EP | 0 610 511 A1 | 8/1994 |
| FR | 2 491 333 A1 | 9/1982 |
| FR | 2 753 626 A1 | 3/1998 |
| FR | 2774595 A1 | 5/1999 |
| WO | WO 2005000241 A2 * | 1/2005 |

OTHER PUBLICATIONS

International Search Report dated Aug. 6, 2007 for corresponding PCT/FR2007/050927 in English.
Structure of clobetasol propionate from Wikipedia accessed on Jun. 6, 2011 at http://en.wikipedia.org/wiki/Clobetasol_propionate.
Structure of fluticasone proprionate from Wikipedia accessed on Jun. 6, 2011 at http://en.wikipedia.org/wiki/Fluticasone_propanoate.

* cited by examiner

*Primary Examiner* — Abigail Fisher
(74) *Attorney, Agent, or Firm* — Dentons US LLP

(57) ABSTRACT

Topically applicable compositions in the form of oil-in-water emulsions contain a pro-penetrating system including at least one glycol and at least one additional pro-penetrating agent, a suitable gelling agent and at least one active agent of the family of steroidal anti-inflammatory agents and are useful, e.g., for the treatment of psoriasis.

6 Claims, No Drawings

TOPICAL ANTI-INFLAMMATORY COMPOSITIONS COMPRISING O/W EMULSIONS CONTAINING PRO-PENETRATING GLYCOLS

CROSS-REFERENCE TO EARLIER APPLICATIONS

This application is a continuation of PCT/FR2007/050927, filed Mar. 14, 2007 and designating the United States (published in the French language on Sep. 20, 2007 as WO 2007/104897 A1; the title and abstract were also published in English), which claims priority under 35 U.S.C. §119 of FR0602284, filed Mar. 15, 2006, each hereby expressly incorporated by reference in its entirety and each assigned to the assignee hereof.

CROSS-REFERENCE TO COMPANION APPLICATION

Copending U.S. patent application Ser. No. 12/232,304, filed concurrently herewith, hereby expressly incorporated by reference and assigned to the assignee hereof.

BACKGROUND OF THE INVENTION

1. Technical Field of the Invention

The present invention relates to novel compositions in the form of an emulsion of oil-in-water (O/W) type for topical application, comprising a novel combination of pro-penetrating agents including at least one glycol, a suitable gelling agent and an active agent of the family of steroidal anti-inflammatory agents.

2. Description of Background and/or Related and/or Prior Art

There currently exist many topical compositions comprising a steroidal anti-inflammatory agent and a high content of glycol, the latter promoting the penetration of the steroidal anti-inflammatory agent into the skin. Given the high content of pro-penetrating glycol, these compositions are formulated in the form of emulsions with a high content of fatty phase, which are also commonly known as "lipocreams", in the form of anhydrous compositions known as "ointments", in the form of fluid compositions with a high content of volatile solvents, such as ethanol or isopropanol, useful for application to the scalp, also known as "hair lotions", or in the form of viscous O/W emulsions, which are also known as "O/W creams".

For example, O/W creams comprising a corticoid and a high percentage of propylene glycol, marketed under the trademark Temovate® by Glaxo, are known. However, the stabilization of a formulation comprising such a percentage of glycol makes it necessary to include in the emulsion emulsifiers and stabilizers of glyceryl stearate or PEG 100 stearate type or, alternatively, stabilizers or consistency factors of white wax or cetostearyl alcohol type, which promote the formation of a thick cream of waxy appearance.

In FR 2 753 626, assigned to the assignee hereof, more fluid emulsions are described containing a corticoid that have a high percentage of propylene glycol. However, since the high percentage of propylene glycol makes it difficult to prepare the emulsion, it is advantageous to have available a novel stable formulation of O/W emulsion type, containing less propylene glycol, which has a non-greasy and non-tacky aspect, while at the same time maintaining the rheological and pro-penetrating properties of the composition.

SUMMARY OF THE INVENTION

The present invention thus features novel pharmaceutical compositions in the form of an emulsion of oil-in-water (O/W) type for topical application, comprising, formulated into a pharmaceutically acceptable vehicle:
a) at least one steroidal anti-inflammatory agent;
b) a pro-penetrating system which comprises at least one glycol and at least one additional pro-penetrating agent;
c) at least one gelling agent;
d) at least one non-polymeric emulsifier;
said compositions not containing any polymeric emulsifier.

DETAILED DESCRIPTION OF BEST MODE AND SPECIFIC/PREFERRED EMBODIMENTS OF THE INVENTION

Among the steroidal anti-inflammatory agents that are exemplary, albeit non-limiting, are hydrocortisone, anthranoids, betamethasone valerate and clobetasol propionate. The steroidal anti-inflammatory agent is preferably clobetasol propionate.

Advantageously, the compositions according to the invention comprise from 0.0001% to 5% by weight and preferably from 0.025% to 1% by weight of active agent relative to the total weight of the composition.

In one preferred embodiment according to the invention, the compositions comprise from 0.025% to 0.5% by weight and preferentially 0.05% by weight of clobetasol propionate relative to the total weight of the composition.

The principal advantage of the compositions according to the invention is to reduce the percentage of propylene glycol employed in the prior art by replacing the latter with a mixture selected such as to provide the desired pro-penetrating properties without encountering the previous difficulties of emulsification and of stabilization of the emulsion caused by the high percentage of propylene glycol.

Thus, the pro-penetrating system according to the invention comprises at least one glycol and at least one additional pro-penetrating agent. The glycols employed according to the invention are: alkylene or polyalkylene glycols. Non-limiting examples include (C1 to C6) alkylene and polyalkylene glycols, such as ethylene glycol, polyethylene glycol (2 to 20 monomers), propylene glycol, dipropylene glycol, butylene glycol, pentylene glycol and hexylene glycol. They may or may not be oxyethylenated (2 to 50 EO). Also exemplary are glycol ethers, such as ethoxydiglycol, diethylene glycol monoethyl ether, marketed under the trademark Transcutol HP by Gattefosse, propylene glycol dipelargonate, propylene glycol laurate marketed under the trademark Lauroglycol by Gattefosse, and propylene glycol dicaprate dicaprylate marketed under the trademark Estol 1526 by Uniqema.

The glycols that are preferred according to the invention are propylene glycol, dipropylene glycol, propylene glycol dipelargonate, propylene glycol laurate, ethoxydiglycol and propylene glycol dicaprate dicaprylate.

The pro-penetrating system also comprises at least one additional pro-penetrating agent.

The said additional pro-penetrating agent is selected from among the glycols listed above and the pro-penetrating agents of the family of fatty esters, fatty acids or fatty alcohols, or alcohols. Such pro-penetrating agents are, in particular, ethanol, dimethyl isosorbide marketed under the trademark Arlasolve DMI by Uniqema, methylpyrrolidone marketed under the trademark Pharmasolve by ISP, oleic acid marketed under the trademark Oléine V2 by Stéarinerie Dubois, PEG-8 capric/caprylic glycerides, marketed under the trademark Labrasol by Gattefosse, and oleyl alcohol marketed under the trademark HD Eutanol V PH by Cognis.

Preferably, the compositions according to the invention comprise one of the following pro-penetrating systems:
propylene glycol and dimethyl isosorbide,
propylene glycol and ethanol,
propylene glycol, diethylene glycol monoethyl ether and propylene glycol laurate,
propylene glycol and methylpyrrolidone,
propylene glycol, dimethyl isosorbide and ethanol,
propylene glycol, methylpyrrolidone and oleyl alcohol.

Preferentially, the compositions according to the invention comprise from 20% to 60% by weight and preferably from 35% to 47% by weight of pro-penetrating glycol, relative to the total weight of the composition, and from 0.5% to 40% by weight and preferentially from 1% to 20% by weight of additional pro-penetrating agent, relative to the total weight of the composition.

The compositions according to the invention are emulsions and thus contain a fatty phase and an aqueous phase.

The fatty phase of the emulsions according to the invention may comprise fatty substances usually employed in the intended field of application.

Among these, exemplary are silicone fatty substances such as silicone oils, and also non-silicone fatty substances such as plant, mineral, animal or synthetic oils.

Among the silicone fatty substances, exemplary are:
(i) poly($C_1$-$C_{20}$)alkylsiloxanes and especially those containing trimethylsilyl endgroups, preferably those with a viscosity of less than 0.06 $m^2/s$, among which exemplary are linear polydimethylsiloxanes and alkylmethylpolysiloxanes such as cetyl dimethicone (CTFA name),
(ii) volatile silicone oils, such as:
cyclic volatile silicones containing from 3 to 8 and preferably from 4 to 5 silicon atoms. They are preferably cyclotetradimethylsiloxane, cyclopentadimethylsiloxane or cyclohexadimethylsiloxane,
cyclocopolymers of the dimethylsiloxane/methylalkylsiloxane type, such as Silicone FZ 3109 marketed by Union Carbide, which is a dimethylsiloxane/methyloctylsiloxane cyclocopolymer,
linear volatile silicones containing from 2 to 9 silicon atoms. They are, for example, hexamethyldisiloxane, hexylheptamethyltrisiloxane or octylheptamethyltrisiloxane,
(iii) phenylsilicone oils, especially those of formula:

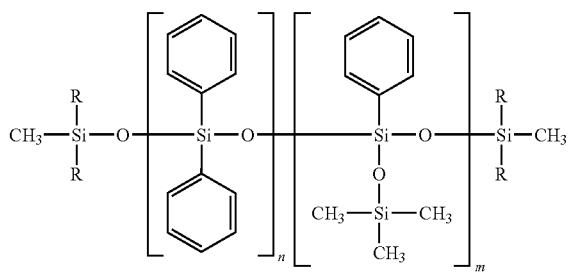

(I)

in which:
R is a C1-C30 alkyl radical, an aryl radical or an aralkyl radical,
n is an integer ranging from 0 to 100,
m is an integer ranging from 0 to 100, with the proviso that the sum thereof ranges from 1 to 100.

Among the non-silicone fatty substances that are exemplary are common oils, such as liquid paraffin, liquid petroleum jelly, sweet almond oil, perhydrosqualene, apricot oil, wheatgerm oil, sweet almond oil, beauty-leaf oil, palm oil, castor oil, avocado oil, jojoba oil, olive oil or cereal germ oil; esters of fatty acids or of fatty alcohols, such as octyldodecyl alcohol or polyalcohol octanoates, decanoates or ricinoleates; fatty acid triglycerides; glycerides; hydrogenated polyisobutene, hydrogenated oils that are solid at 25° C.; lanolins; fatty esters that are solid at 25° C.

These fatty substances may be selected in particular in a varied manner by one skilled in this art in order to prepare a composition having the desired properties, for example in terms of consistency or texture.

Thus, the fatty phase of the emulsions according to the invention may be present in a content of from 5% to 50% by weight and preferably from 15% to 25% by weight relative to the total weight of the composition.

The aqueous phase of the emulsions according to the invention may comprise water, a floral water such as cornflower water, or a natural spring or mineral water selected, for example, from l'eau de Vittel, waters from the Vichy basin, l'eau d'Uriage, l'eau de la Roche Posay, l'eau de Bourboule, l'eau d'Enghien-les-Bains, l'eau de Saint Gervais-les-Bains, l'eau de Néris-les-Bains, l'eau d'Allevard-les-Bains, l'eau de Digne, l'eau de Maizières, l'eau de Neyrac-les-Bains, l'eau de Lons-le-Saunier, les Eaux Bonnes, l'eau de Rochefort, l'eau de Saint Christau, l'eau de Fumades, l'eau de Tercis-les-bains, l'eau d'Avène or l'eau d'Aix les Bains.

The said aqueous phase may be present in a content of from 10% to 70% by weight and preferably from 20% to 40% by weight relative to the total weight of the composition.

One of the additional advantages of the present invention is that of providing compositions in the form of a stable emulsion without employing standard polymeric emulsifiers. The reason for this is that the emulsifiers conventionally employed in the prior art are polymeric emulsifiers of Pemulen type. Such emulsions have the drawback of being sensitive to electrolytes. Thus, in the present invention, the said crosslinked polymers of Pemulen type, and especially the products marketed by Goodrich under the trademarks Pemulen TR1, Pemulen TR2, Carbopol 1342 or Carbopol 1382, are not used; these polymers, of acrylate/C10-30 alkyl acrylate crosspolymer type, which are copolymers comprising a major fraction of acrylic acid and a minor fraction of $C_{10}$-$C_{30}$ (meth)acrylic acid esters, are thus excluded from the present invention.

Specifically, it has now been found that the stability of the desired composition is provided without adding any polymeric emulsifying compound. The stable emulsions according to the invention are obtained in the presence of a system composed of a gelling agent and a non-polymeric emulsifier.

According to the invention, the term "stable composition" means an emulsion that is physically and chemically stable over time.

According to the invention, the term "physical stability" means a composition that does not present any macroscopic change of appearance (phase separation, change in color of appearance, etc.) or microscopic change of appearance (re-crystallization of the active agent) after storage at temperatures of 25° C. (=room temperature: RT), 4° C. and 40° C., for 3 months.

According to the invention, the term "chemical stability" means a composition in which the content of active principle remains stable after three months at room temperature and at 40° C. A stable content of active principle means according to the invention that the content shows very little variation relative to the initial content, i.e., the variation in the content of active principle at time T should not be less than 90% to more particularly than 95% of the initial content at T0.

The compositions according to the invention thus comprise at least one gelling agent and/or thickener in preferential concentrations of from 0.1% to 5% by weight relative to the total weight of the composition.

Among the possible gelling agents, non-limiting examples thereof include:

polysaccharide biopolymers, for instance xanthan gum such as Keltrol T and Xantural 180 marketed by Kelco, carob gum, guar gum, alginates, modified celluloses such as hydroxyethylcellulose, methylcellulose or hydroxypropylcellulose such as the product marketed under the trademark Natrosol HHX 250 by Aqualon, hydroxypropylmethylcellulose (this type of water-soluble polymer has viscosity-enhancing, viscoelastic, gelling and suspending properties) and carboxymethylcellulose, carbomers, for instance Carbopol 981 marketed by BF Goodrich and the Carbopol Ultrez 10 marketed by Noveon, starch derivatives, such as Structure XL marketed by National Starch, and mixtures thereof.

Preferably, according to the invention, the gelling agents are carbomers and/or xanthan gums.

Moreover, the compositions according to the invention may comprise from 0.01% to 3% by weight and preferably from 0.1% to 2% by weight, relative to the total weight of the composition, of at least one non-polymeric emulsifier, which, by reducing the surface tension of the dispersed phase, will allow adjustment of the droplets of the emulsion.

The non-polymeric emulsifiers according to the invention are emulsifiers conventionally employed in water-in-oil (W/O) emulsions. However, in the presence of at least one gelling agent, such emulsifiers allow oil-in-water (O/W) emulsions according to the invention to be obtained.

Such non-polymeric emulsifiers may be selected from among esters of saturated or unsaturated, natural or synthetic fatty acids, especially of oleic acid or (iso)stearic acid, such as the polyglyceryl esters of isostearic acid marketed under the trademark Lameform TGI by Sidobre-Sinnova Henkel, sorbitan isostearate marketed under the trademark Arlacel 987 by Uniqema, sorbitan sesquioleate marketed under the trademark Arlacel 83 by Uniqema, sorbitan laurate marketed under the trademark Span 20 by Uniqema, esters of glycol and of isostearic acid, for instance PEG-6 isostearate marketed under the trademark Olepal Isostearique by Gattefosse, esters of sorbitol and of oleic acid, for instance the polysorbates marketed under the trademark Tween by Uniqema, fatty alcohol ethers, especially of oleyl alcohol, in particular esters of glycol and of oleyl alcohol, for instance the oleth products marketed under the trademark Brij by Uniqema, oxyethylenated sorbitan monostearate, and fatty alcohols such as stearyl alcohol or cetyl alcohol.

Sorbitan esters or polyglycerol esters will preferably be employed according to the invention.

Preferentially, the compositions according to the invention will comprise from 0.05% to 5% by weight and even more preferentially from 1% to 2% by weight of sorbitan esters or of polyglycerol esters, relative to the total weight of the composition.

In one particular embodiment according to the invention, it has been found, surprisingly, that emulsions containing both a carbomer and a xanthan gum in the presence of a non-polymeric emulsifier show good physical and chemical stability, even in the absence of polymeric emulsifier.

The pH of the compositions according to the invention advantageously ranges from 5 and 7.5 and preferably from 5.5 and 6.5. It will be adjusted to the desired value by adding common mineral or organic acids or bases.

The emulsions may also comprise any additive usually included in cosmetics or pharmaceuticals, such as antioxidants, dyes, fragrances, essential oils, preservatives, cosmetic active agents, moisturizers, vitamins, essential fatty acids, sphingolipids, self-tanning compounds such as DHA, sunscreens, liposoluble and especially hydrocarbon-based polymers, such as polybutene, polyalkylenes, polyacrylates and silicone polymers that are compatible with fatty substances. Needless to say, one skilled in this art will take care to select this or these optional additional compound(s), and/or the amount thereof, such that the advantageous properties of the composition according to the invention are not, or are not substantially, adversely affected by the envisaged addition.

These additives may be present in the composition in a proportion of from 0 to 10% by weight relative to the total weight of the composition.

The present invention also features administration of the subject compositions for the treatment of psoriasis, whether regime or regimen.

Preferably, according to the invention, the composition comprises, formulated into a pharmaceutically acceptable vehicle:
  0.0025% to 0.5% of clobetasol propionate,
  30% to 50% of a pro-penetrating glycol,
  1% to 20% of at least one additional pro-penetrating agent,
  0.1% to 5% of at least one gelling agent,
  0.1% to 5% of non-polymeric emulsifier.

More preferably, according to the invention, the composition comprises, formulated into a pharmaceutically acceptable vehicle:
  0.0025% to 0.5% of clobetasol propionate,
  30% to 50% of a pro-penetrating glycol,
  1% to 20% of at least one additional pro-penetrating agent,
  0.1% to 5% of two gelling agents,
  0.1% to 5% of non-polymeric emulsifier.

In a particularly preferred embodiment, the composition according to the invention comprises:
  a. 0.0025% to 0.5% of clobetasol propionate,
  b. 30% to 50% of a glycol selected from among propylene glycol, dipropylene glycol, propylene glycol dipelargonate, propylene glycol laurate, ethoxydiglycol and propylene glycol dicaprate-dicaprylate,
  c. 1% to 20% of at least one additional pro-penetrating agent selected from among propylene glycol, dipropylene glycol, propylene glycol dipelargonate, propylene glycol laurate, ethoxydiglycol, propylene glycol dicaprate-dicaprylate, ethanol, dimethyl isosorbide, methylpyrrolidone, oleic acid, PEG-8 capric/caprylic glycerides, and oleyl alcohol,
  d. 0.1% to 5% of at least one gelling agent selected from among xanthan gum, carob gum, guar gum, alginates, hydroxyethylcellulose, methylcellulose, hydroxypropylcellulose, hydroxypropylmethylcellulose, carboxymethylcellulose, carbomers and starch derivatives, and mixtures thereof,
  e. 0.1% to 5% of non-polymeric emulsifier selected from among polyglyceryl esters of isostearic acid, sorbitan isostearate, sorbitan sesquioleate, sorbitan laurate, glycol esters of isostearic acid, sorbitol esters of oleic acid, glycol esters of oleyl alcohol, oxyethylenated sorbitan monostearate, stearyl alcohol and cetyl alcohol.

In order to further illustrate the present invention and the advantages thereof, the following specific examples are given, it being understood that same are intended only as illustrative and in nowise limitative. In said examples to follow, all parts and percentages are given by weight, unless otherwise indicated.

Formulation Example 1

| | |
|---|---|
| water | qs 100 |
| carbomer | 0.28% |
| xanthan gum | 0.10% |
| active agent | 0.05% |
| propylene glycol | 45.50% |
| oleyl alcohol | 1.00% |
| methylpyrrolidone | 1.00% |
| sorbitan laurate | 2.00% |
| liquid paraffin | 20.00% |
| sodium hydroxide | qs pH 6 |

| | | T0: fluid white milk pH = 5.66 Centrifuge.: 10,000 rpm: no comments Micro.: globule size 5 to 7.5 μm | | |
|---|---|---|---|---|
| | | T1 month | T2 months | T3 months |
| RT | Macroscopic appearance pH | Fluid white milk, in accordance with T0 pH 5.72 | Fluid white milk, in accordance with T0 pH 5.51 | Fluid white milk, in accordance with T0 pH 5.51 |
| | Microscopic appearance | Globule size 5 to 7.5 μm | Globule size 5 to 7.5 μm | Globule size 5 to 7.5 μm |
| | Assay of the active agent (HPLC) T0: 99.1% | 99.1% | 99.4% | 96.6% |
| 4° C. | Macroscopic appearance | Fluid white milk, in accordance with T0 | Fluid white milk, in accordance with T0 | Fluid white milk, in accordance with T0 |
| | Microscopic appearance | Globule size 5 to 7.5 μm | Globule size 5 to 7.5 μm | Globule size 5 to 7.5 μm |
| 40° C. | Macroscopic appearance | Fluid white milk, in accordance with T0 | Fluid white milk, in accordance with T0 | Fluid white milk, in accordance with T0 |
| | Assay of the active agent (HPLC) T0: 99.1% | 98.7% | 98.2% | 96.5% |

Formulation Example 2

| | |
|---|---|
| water | qs 100 |
| carbomer | 0.28% |
| xanthan gum | 0.10% |
| active agent | 0.05% |
| propylene glycol | 37.50% |
| ethanol | 5.00% |
| dimethyl isosorbide | 5.00% |
| sorbitan laurate | 2.00% |
| liquid paraffin | 20.00% |
| sodium hydroxide | qs pH 6 |

| | | T0: fluid white milk pH = 5.73 Centrifuge.: 10,000 rpm: no comments Micro.: globule size 5 to 7.5 μm | | |
|---|---|---|---|---|
| | | T1 month | T2 months | T3 months |
| RT | Macroscopic appearance pH | Fluid white milk, in accordance with T0 pH 5.78 | Fluid white milk, in accordance with T0 pH 5.57 | Fluid white milk, in accordance with T0 pH 5.73 |
| | Microscopic appearance | Globule size 5 to 7.5 μm | Globule size 5 to 7.5 μm | Globule size 5 to 7.5 μm |
| | Assay of the active agent (HPLC) T0: 99.7% | 99% | 99.2% | 97.7% |
| 4° C. | Macroscopic appearance | Fluid white milk, in accordance with T0 | Fluid white milk, in accordance with T0 | Fluid white milk, in accordance with T0 |
| | Microscopic appearance | Globule size 5 to 7.5 μm | Globule size 5 to 7.5 μm | Globule size 5 to 7.5 μm |
| 40° C. | Macroscopic appearance | Fluid white milk, in accordance with T0 | Fluid white milk, in accordance with T0 | Fluid white milk, in accordance with T0 |
| | Assay of the active agent (HPLC) T0: 99.7% | 98.8% | 98.3% | 94.5% |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable pharmaceutical composition comprising a physically and chemically stable oil-in-water emulsion which comprises:

(a) 0.0025% to 0.5% of clobetasol propionate, said clobetasol propionate being the only active ingredient in the composition;

(b) a pro-penetrating system which consists of 30% to 50% of at least one glycol selected from the group consisting of propylene glycol, ethylene glycol, butylene glycol, pentylene glycol, hexylene glycol, diethylene glycol monoethyl ether, dipropylene glycol, propylene glycol dipelargonate, propylene glycol laurate, ethoxydiglycol and propylene glycol dicaprate/dicaprylate and 1% to 20% of at least one additional pro-penetrating agent selected from the group consisting of propylene glycol, dipropylene glycol, propylene glycol dipelargonate, propylene glycol laurate, ethoxydiglycol, propylene glycol dicaprate-dicaprylate, ethanol, dimethyl isosorbide, methylpyrrolidone, oleic acid, PEG-8 capric/caprylic glycerides and oleyl alcohol; said pro-penetrating system being the only pro-penetrating system in the composition;

(c) 0.1% to 5% of at least one gelling agent selected from the group consisting of xanthan gum, carob gum, guar gum, alginates, hydroxyethylcellulose, methylcellulose, hydroxypropylcellulose, hydroxypropylmethylcellulose, carboxymethylcellulose, carbomers and starch derivatives, and mixtures thereof, said at least one gelling agent being the only gelling agent(s) in the composition;

(d) 0.1% to 5% of at least one emulsifier which is selected from the group consisting of polyglyceryl esters of isostearic acid, sorbitan isostearate, sorbitan sesquioleate, sorbitan laurate, glycol esters of isostearic acid, sorbitol esters of oleic acid, glycol esters of oleyl alcohol, oxyethylenated sorbitan monostearate, stearyl alcohol and cetyl alcohol, said at least one emulsifier being the only emulsifier(s) in the composition;

(e) an oil, (f) water, and (g) optionally, sodium hydroxide, for adjusting the pH of the emulsion to from 5 to 7.5;

said composition being devoid of any copolymer comprising a major fraction of acrylic acid and a minor fraction of $C_{10}$-$C_{30}$ (meth)acrylic acid esters, and wherein all percents are by weight with respect to the total weight of the composition.

2. The pharmaceutical composition/oil-in-water emulsion as defined by claim 1, said pro-penetrating system consisting of:

(a) propylene glycol and dimethyl isosorbide, (b) propylene glycol and ethanol, (c) propylene glycol, diethylene glycol monoethyl ether and propylene glycol laurate, (d) propylene glycol and methylpyrrolidone, (e) propylene glycol, dimethyl isosorbide and ethanol, or (f) propylene glycol, methylpyrrolidone and oleyl alcohol.

3. The pharmaceutical composition/oil-in-water emulsion as defined by claim 1, wherein said at least one glycol is:

propylene glycol, dipropylene glycol, propylene glycol dipelargonate, propylene glycol laurate, ethoxydiglycol or propylene glycol dicaprate-dicaprylate.

4. A regime or regimen for the treatment of psoriasis, comprising topically applying onto the affected skin area of an individual afflicted therewith, a thus effective amount of the pharmaceutical composition/oil-in-water emulsion as defined by claim 1.

5. The pharmaceutical composition/oil-in-water emulsion as defined by claim 1, wherein the propenetrating system consists of propylene glycol, oleyl alcohol, and methylpyrrolidone; the at least one emulsifier consists of sorbitan laurate; the at least one gelling agent consists of carbomer and xanthan gum, and the oil consists of liquid paraffin.

6. The pharmaceutical composition/oil-in-water emulsion as defined by claim 1, wherein the propenetrating system consists of propylene glycol, ethanol and dimethyl isosorbide; the at least one emulsifier consists of sorbitan laurate; the at least one gelling agent consists of carbomer and xanthan gum, and the oil consists of liquid paraffin.

* * * * *